US011154216B2

(12) United States Patent
Dreyer et al.

(10) Patent No.: US 11,154,216 B2
(45) Date of Patent: Oct. 26, 2021

(54) DEVICE FOR DETERMINING THE CONCENTRATION OF AT LEAST ONE GAS COMPONENT IN A BREATHING GAS MIXTURE

(71) Applicant: Drägerwerk AG & Co. KGaA, Lübeck (DE)

(72) Inventors: Peter Dreyer, Pansdorf (DE); Günter Steinert, Bad Oldesloe (DE); Bernd-Michael Dicks, Damlos (DE); Ralph-Peter Jacobi, Reinbek (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 1035 days.

(21) Appl. No.: 15/796,012

(22) Filed: Oct. 27, 2017

(65) Prior Publication Data

US 2018/0116555 A1 May 3, 2018

(30) Foreign Application Priority Data

Oct. 28, 2016 (DE) ...................... 10 2016 012 971.9

(51) Int. Cl.
*A61B 5/083* (2006.01)
*A61B 5/08* (2006.01)
(Continued)

(52) U.S. Cl.
CPC ............ *A61B 5/0836* (2013.01); *A61B 5/082* (2013.01); *G01J 3/021* (2013.01); *G01J 3/42* (2013.01); *G01J 3/427* (2013.01); *G01N 21/314* (2013.01); *G01N 21/3504* (2013.01); *G01J 2003/1239* (2013.01); *G01J 2003/2806* (2013.01); *G01N 2021/052* (2013.01)

(58) Field of Classification Search
CPC ......... A61B 5/0836; A61B 5/082; G01J 3/427
See application file for complete search history.

(56) References Cited

U.S. PATENT DOCUMENTS 5,261,415 A 11/1993 Dussault
5,341,214 A 8/1994 Wong
(Continued)

FOREIGN PATENT DOCUMENTS

DE 100 47 728 B4 12/2005
DE 602 21 346 T2 4/2008
(Continued)

*Primary Examiner* — Daniel L Cerioni
*Assistant Examiner* — Yasmeen S Warsi
(74) *Attorney, Agent, or Firm* — McGlew and Tuttle, P.C.

(57) ABSTRACT

A device (1) for determining the concentration of a gas component is configured with a radiation source (30) for radiating (31) light as a light emission in an infrared wavelength range. Two detector arrays (52, 62) with two detector elements (50, 60) are configured suitably for detecting the light emission generated by the radiation source (30) in two detector arrays (52, 62). Two filter elements (51, 61) are associated with the detector elements (50, 60). The two detector elements (50, 60) are oriented in relation to the radiation source, so that a range of overlap (65) is obtained due to the two detector arrays (52, 62). The range of overlap (65) causes attenuations in the propagation of light, which may be due to gas molecules or moisture (400). The attenuations in the propagation of light affect both detector elements (50, 60) and are compensated concerning the determination of the concentration.

15 Claims, 5 Drawing Sheets

(51) Int. Cl.
    *G01N 21/31*     (2006.01)
    *G01J 3/42*     (2006.01)
    *G01J 3/02*     (2006.01)
    *G01J 3/427*     (2006.01)
    *G01N 21/3504*     (2014.01)
    G01N 21/05     (2006.01)
    G01J 3/28     (2006.01)
    G01J 3/12     (2006.01)

(56) References Cited

U.S. PATENT DOCUMENTS

| | | |
|---|---|---|
| 6,469,303 B1 | 10/2002 | Sun et al. |
| 2011/0109905 A1 | 5/2011 | Martin |

FOREIGN PATENT DOCUMENTS

| | | |
|---|---|---|
| EP | 0 536 727 B1 | 12/1994 |
| EP | 2 169 369 A1 | 3/2010 |
| GB | 1 586 622 A | 3/1981 |
| WO | 2015/010709 A1 | 1/2015 |

DEVICE FOR DETERMINING THE CONCENTRATION OF AT LEAST ONE GAS COMPONENT IN A BREATHING GAS MIXTURE

CROSS REFERENCE TO RELATED APPLICATIONS

This application claims the benefit of priority under 35 U.S.C. § 119 of German Application 10 2016 0129 71.9, filed Oct. 28, 2016, the entire contents of which are incorporated herein by reference.

FIELD OF THE INVENTION

The present invention pertains to a device for determining the concentration of at least one gas component in a breathing gas mixture.

BACKGROUND OF THE INVENTION

Devices for determining the concentrations of gas components in a breathing gas mixture are used, among other things, to determine concentration values of carbon dioxide exhaled by patients. DE 100 47 728 B4 describes a sensor for measuring carbon dioxide, laughing gas and anesthetic gases. A device comprising four optical filter elements with associated detector elements is shown. The combinations of filter and detector elements are arranged around a beam-mixing system. Such a beam-mixing system, shown in a configuration in a multispectral sensor, is shown in EP 0 536 727 B1. Such a sensor system is used in routine clinical practice, for example, in a capnograph as well as in a so-called $CO_2$ mainstream sensor or also in a $CO_2$ sidestream sensor. U.S. Pat. No. 5,261,415 B2 shows a $CO_2$ mainstream capnography sensor. An insert, in which an infrared optical measuring system is, in turn, arranged, is arranged in a cuvette, which carries the breathing gas. EP 0 536 727 B1 shows the complicated manner in which optical components must be arranged and configured in order to achieve an effective beam mixing. The beam mixing has the task of allowing locally occurring contaminations to become effective symmetrically in both the reference channel and the measuring channel. This is necessary to ensure that the ratio of the measuring channel to the reference channel is guaranteed at all working points such that contaminations, water vapor as well as aging effects of the detector elements can be permanently compensated during the operation. The drawback of the solution is, as is shown in EP 0 536 727 B1, that the beam mixing brings about a signal weakening due to the infrared light having to be deflected and reflected in the measuring cuvette several times. This signal weakening leads to a worse signal-to-noise ratio (SNR). This makes it then necessary to compensate a reduction of the measured signal by means of increasing the absorption length in order to attain the necessary measured value resolution. An increase in the absorption lengths results in an enlargement of the physical configuration. The requirement for beam mixing and for the plurality of components involved in it is, furthermore, disadvantageous in terms of the complexity and high tolerance requirements of the components involved (tolerance chain) as well as the high manufacturing costs resulting therefrom for a multispectral sensor of the type proposed in EP 0 536 727 B1.

SUMMARY OF THE INVENTION

Based on the above-described state of the art and the drawbacks described in this connection, an object of the present invention is to provide a device for determining the gas concentration of at least one gas component in a breathing gas mixture, which is characterized by a small space requirement as well as comparatively favorable manufacturing costs.

The following components are provided according to the present invention in the device for determining the concentration of at least one gas component in a breathing gas mixture: a radiation source suitable for and configured to radiate by means of a radiating surface a light emission in a wavelength range of lambda1 ($\lambda 1$)=2,500 nm to lambda2 ($\lambda 2$)=14,000 nm, two detector arrays with two detector elements configured suitably for detecting the light emission generated by the radiation source and with two bandpass filter elements arranged at the detector elements, a diaphragm element B, a flow channel with a first light transmission element F1 and with a second light transmission element F2, and a control unit.

The light emitted by the radiation source is emitted essentially at right angles from the radiating surface in the direction of a vertical (length) axis of the device.

The wavelength range of lambda1 ($\lambda 1$)=2.5 µm to lambda2 ($\lambda 2$)=14.0 µm of the radiation source makes possible an infrared optical measurement of laughing gas concentrations, carbon dioxide concentrations as well as different hydrocarbons, for example, volatile anesthetic gases or methane.

The detector elements are configured, for example, as semiconductor detectors, pyroelectric detectors (pyrodetectors), thermoelectric detectors (thermopiles, thermocouples), as heat detectors (bolometers) as well as as combinations of semiconductor detectors and heat detectors. The detector elements are configured for detecting light for an infrared radiation in infrared wavelength ranges, in which absorption by gases, for example, carbon dioxide, typically occurs.

The bandpass filter elements are configured, for example, as optical interference filters in the form of interference layers on a substrate. These transmit light in a wavelength range defined by an absorption range of a measured gas in a range of lambda1 ($\lambda 1$)=2.5 µm to lambda2 ($\lambda 2$)=14.0 µm.

The light transmission elements F1, F2 may be made of glass material, plastic material in the form of a pane or film. The light transmission elements F1, F2 are inserted opposite each other in walls of the flow channel in a gas-tight manner. The light transmission elements F1, F2 are configured for passing through light in a wavelength range of lambda1 ($\lambda 1$)=2.5 µm to lambda2 ($\lambda 2$)=14.0 µm.

The arrangement of the bandpass filter elements is configured such that the infrared radiation emitted by the radiation source passes through two bandpass filter elements each in front of the two detector elements in a direct beam path or also on an indirect beam path, for example, by means of a deflection of the infrared radiation by reflective elements or mirror arrays in the beam path.

At least one of the two bandpass filter elements is configured as a filter element optically transparent for an infrared radiation, which is absorbed by the measured gas, in a wavelength range.

The detector element at which this bandpass filter element is arranged represents the so-called measuring channel in the device for determining the concentration of at least one gas component in a breathing gas mixture.

At least one of the two bandpass filter elements is configured as being optically transparent for an infrared radiation, which is not absorbed or is only slightly absorbed by the measured gas, in a wavelength range.

The detector element at which this bandpass filter element is arranged represents the so-called reference channel in the device for determining the concentration of at least one gas component in a breathing gas mixture.

In the two detector arrays, the two detector elements form two detector surfaces with the two bandpass filter elements arranged at the detector elements at the surfaces thereof. The detector surfaces are used to receive the light emission generated by the radiation sources to the detector elements. The bandpass filter elements are used to filter the light generated by the radiation source as well as to pass it on to the detector elements.

Typical measured gases, often also called target gases, are, for example, carbon dioxide or laughing gas as well as a plurality of gaseous organic compounds, such as methane, or volatile anesthetic gases, for example, halothane, isoflurane, desflurane and enflurane.

The bandpass filter elements are configured for the optical filtering of infrared light in a transmission range of a wavelength range of 2.5 µm to 14 µm.

Thus, transmission ranges as shown in Table 1 below are made possible for gases with such bandpass filter elements.

TABLE 1

| No. | Gas species | Wavelength range | |
|---|---|---|---|
| 1 | Carbon dioxide | 4.2 µm to 4.4 µm | $CO_2$ |
| | Laughing gas | 7.8 µm to 9.0 µm | $N_2O$ |
| | Methane | 3.1 µm to 3.5 µm | $CH_4$ |
| | Ethane | 3.2 µm to 3.6 µm | $C_2H_5$ |
| | Halothane | 8 µm to 10 µm | $C_2HBrClF_3$ |
| | Isoflurane | 8 µm to 10 µm | $C_3H_2OClF_5$ |
| | Enflurane | 8 µm to 10 µm | $C_3H_2ClF_5O$ |
| | Sevoflurane | 8 µm to 10 µm | $C_4H_3F_7O$ |
| | Desflurane | 8 µm to 10 µm | $C_3H_2F_6O$ |
| | Acetone | 8 µm to 10 µm | $C_3H_6O$ |
| | Ethyl alcohol | 8 µm to 10 µm | $C_2H_5OH$ |

The gases laughing gas, halothane, sevoflurane and desflurane are used when anesthesia is performed, for example, during surgical procedures to anesthetize patients. Acetone is formed as a possible metabolite in patients and is thus contained, for example, in the air exhaled by diabetics. Ethyl alcohol may be present, for example, in the air exhaled by patients who are under the influence of alcohol.

Measured values from the measuring channel and the reference channel are detected by means of the control unit in the device for determining the concentration of at least one gas component in a breathing gas mixture and they are related to one another. A quotient of detected measured values of the measuring channel to detected measured values of the reference channel is usually formed, and this quotient indicates an indicator of a concentration of the measured gas in the concentration-measuring device, i.e., the concentration of a quantity of gas that is present in the beam path.

The arrangement in space of the detector elements with bandpass filter elements arranged thereon and of the bandpass filter elements in relation to one another and the arrangement in space of the detector elements with the bandpass filter elements arranged thereon and of the bandpass filter elements form two detector arrays as a detector configuration according to the present invention.

A radiating element or a reflecting optical element, which either emits quantities of light directly in the direction of and onto the two detector arrays or guides quantities of light indirectly by means of reflection in the direction of the two detector arrays in the direction of and onto the detector arrays, is arranged according to the present invention opposite the two detector arrays.

An optically radiating element for a direct radiation of the quantities of light in the direction of and onto the two detector arrays is the radiation source.

An optically reflecting unit for indirectly guiding the quantities of light in the direction of and onto the detector arrays is a reflector device, a reflection element or an optically reflecting mirror, which reflector element is arranged in the device for determining the concentration of at least one gas component in a breathing gas mixture, for example, opposite the two detector arrays. A reflection element or a mirror may be made of a glass material, plastic material in the form of a pane or film.

The control unit, the radiation source and the arrangement in space of the two detector arrays in relation to the radiation source form according to the present invention the device for determining the concentration of at least one gas component in breathing gas mixture.

The arrangement in space of the detector arrays in relation to the radiation source is configured according to a first aspect of the present invention in such a manner that the detector arrays with the two detector elements and with the two bandpass filter elements arranged at the two detector elements are arranged adjacent to one another on the same side of the radiation source.

The arrangement in space of the detector arrays in relation to the radiation source is configured according to another aspect of the present invention in such a manner that the detector arrays with the two detector elements and with the two bandpass filter elements arranged at the two detector elements are arranged opposite the radiation source.

In a first embodiment according to the present invention according to the first aspect of the present invention, the two detector arrays with the two detector elements and with the two bandpass filter elements arranged at the two detector elements are arranged opposite the radiation source at a third distance $l_3$ (a radiation source distance), preferably in a range of 0.1 mm to 10.0 mm.

In a second embodiment according to the present invention according to the other aspect, the detector arrays with the two detector elements and with the two bandpass filter elements arranged at the two detector elements are arranged on the same side adjacent to the radiation source.

The radiation source is arranged essentially centrally between the two detector elements with the two bandpass filter elements arranged at the two detector elements such that it is also integrated in the detector arrays.

At least one optically reflecting element, preferably an optically reflecting element having a flat configuration, which is configured by means of a reflection surface to reflect the quantity of light reaching the reflection surface from the radiation source in the direction of the two detector arrays, is arranged opposite the radiation source and opposite the two detector arrays in this second embodiment according to the present invention at a third distance $l_{3'}$, preferably in a range of 0.1 mm to 5.0 mm.

A horizontal distance $l_0$ preferably in a range of 0.1 mm to 10 mm is selected according to the present invention according to the first and second embodiments between the measuring channel detector element/bandpass filter element and the reference channel detector element/bandpass filter element in the arrangement of the two detector arrays of the measuring channel detector element/bandpass filter element and reference channel detector element/bandpass filter element.

According to the first and second embodiments, a distance between the two detector arrays and the opposite, optically radiating (radiation source) or optically reflecting element is adapted according to the present invention to the dimensioning in terms of the length, width, height of the other components and to the respective flat dimensions of the components (detector elements, bandpass filter elements, radiating surface of the radiating surface, reflection surface of the optically reflecting element) of the device for determining the concentration of at least one gas component in a breathing gas mixture such that the device for determining the concentration of at least one gas component in a breathing gas mixture is obtained as a compact arrangement.

In the sense of the present invention, a compact arrangement of the device for determining the concentration of at least one gas component in a breathing gas mixture is defined as an arrangement whose measuring volume is in a range of 0.05 mL to 0.2 mL and whose greatest structural extension in terms of length, width or height is in a range of 2 mm to 10 mm.

This leads to the advantage that by forming a compact arrangement of the components of the device for determining the concentration of at least one gas component in a breathing gas mixture, a range of overlap is obtained between the beam paths directed from the radiation source or from the optically reflecting element to the two detector elements in a simple manner and without additional elements for radiation deflection or for generating multiple reflection.

This range of overlap arises from the geometry of the arrangement of the two detector arrays with the two detector elements with the bandpass filter elements arranged thereon and with the radiation source and the optically reflecting element. This range of overlap is obtained at right angles from the plane in which the detector elements are arranged in the direction of the radiation source and the optically reflecting element. This range of overlap acts similarly to a beam mixing, but without having to accept the disadvantages that are associated with the beam mixing, namely, the signal weakening caused by the multiple deflections and the unfavorable signal-to-noise ratio (SNR) associated therewith. The range of overlap thus quasi replaces the function of beam mixing, as it is employed, for example, in the above-mentioned EP 0 536 727 B1, i.e., to allow locally occurring contaminations to become effective symmetrically in both the reference channel and the measuring channel, without the drawbacks mentioned above in connection with EP 0 536 727 B1. The range of overlap makes possible the measurement of at least one gas component in a breathing gas mixture, which is essentially insensitive to effects such as the effects of moisture (condensate, water vapor) or impurities. The range of overlap in the compact arrangement of the components ensures that the ratio of the signals of the measuring channel to those of the reference channel is guaranteed at all working points, such that contaminations, water vapors well as aging effects of the detector elements can be permanently compensated during the operation of the device for determining the concentration of at least one gas component in a breathing gas mixture. Due to this geometry of the configuration, for example, gas molecules, water vapor, condensate or also other contaminants, for example, dust, are present in the beam paths of both detector elements, so that the effect of water vapor, condensate or also other contaminants is reflected in the measured signal, for example, as an amplitude attenuation of the measured value, in both the measuring channel and the reference channel. This leads to the possibility of eliminating the effect of moisture (water vapor, condensate) or also of other contaminants by forming the ratio of the signals of the reference channel and of the measuring channel, because the effect on the signals of the reference channel and of the measuring channel is nearly equal and acts with the same effect.

The range of overlap can be defined by selecting the geometries of the measuring channel detector element/bandpass filter element and of the reference channel detector element/bandpass filter element in relation to one another as well as the distance from one another.

According to the first embodiment, the configuration of the range of overlap with extension in space, flat overlap, effective overlap volume for the measuring gas can be further varied and defined in conjunction with a selection of a vertical distance between the radiation source and the arrangements of the measuring channel detector element/bandpass filter element and reference channel detector element/bandpass filter element in relation to one another.

According to the second embodiment, the configuration of the range of overlap with extension in space, flat overlap, effective overlap volume for the measured gas can be further varied and defined in conjunction with a selection of a vertical distance between the optically reflecting element and the arrangements of the measuring channel detector element/bandpass filter element and reference channel detector element/bandpass filter element in relation to one another.

To define suitable configurations of the compact arrangement of the device for determining the concentration of at least one gas component in a breathing gas mixture, configurations are selected by means of ratios, e.g., in the form of quotients of distances between the components, as well as of structural extensions thereof. Structural extensions are defined in the sense of the present invention as horizontal extensions of components in terms of length l or width b, the lengths l being directed at right angles the widths in a Cartesian coordinate system. Quadratic extensions are obtained in this connection when selecting identical length l and width b as well as circular extensions with a diameter d instead of the length l and width b are obtained as special forms.

The definitions for suitable configurations of the compact arrangements are explained in Tables 2a and 2b on the basis of ratios of lengths and distances.

TABLE 2a

| Distance between | Designation |
|---|---|
| the reflection surface of the optically reflecting element and the detection surfaces of the detector arrays | $l_3$ |
| the radiating surface of the radiation source and the detection surfaces of the detector arrays (radiation source distance) | $l_3$ |
| the diaphragm element B and the detection surfaces of the detector arrays | $l_{DB}$ |
| the first light transmission element F1 and the radiating surface of the radiation source | $l_{F1}$ |
| the first light transmission element F1 and the reflection surface of the optically reflecting element | $l_{F1}$ |
| the second light transmission element F2 and the detection surfaces of the detector arrays | $l_{F2}$ |
| horizontal (width) distance between the measuring channel detector element/bandpass filter element and the reference channel detector element/bandpass filter element | $l_0$ |

TABLE 2b

| Extension/horizontal extension (length/diameter) | Designation |
|---|---|
| of the diaphragm element | $l_B$ |
| of the radiation source | $l_S$ |
| of the optically reflecting element | $l_R$ |
| of the two detector arrays (reference channel, measuring channel) | $l_{D1,2}$ |

A compact arrangement of the device for determining the concentration of a gas component is obtained according to first embodiment of the present invention with a radiation source suitable and configured for radiating a light emission in a wavelength range of lambda1 ($\lambda 1$)=2.5 µm to lambda2 ($\lambda 2$)=14.0 µm, with two detector arrays, with two detector elements configured suitably for detecting the light emission generated by the radiation source, with two bandpass filters, which are arranged at the two detector elements and which form detection surfaces for detecting the light emission generated by the radiation source, with a flow channel, which is configured for guiding the flow of a gas flow essentially at right angles to a vertical axis of the light emission, with a first light transmission element F1 and with a second light transmission element F2, which are both configured as optically transparent elements for the light emission in a wavelength range of lambda1 ($\lambda 1$)=2.5 µm to lambda2 ($\lambda 2$)=14.0 µm, with a diaphragm element B for guiding the light beam from the radiation source to the detection surfaces of the two detector arrays, and with a control unit for controlling the operation of the radiation source and for detecting the signals of the two detector elements.

One of the two bandpass filter elements is configured as being optically transparent for an infrared radiation that is absorbed by a measured gas, and one of the two bandpass filter elements for an infrared radiation is configured as being optically transparent for a radiation that is not absorbed by the measured gas.

One radiating surface of the radiation source is arranged at a vertical distance $l_3$ (33) from the two detector surfaces of the two detector arrays.

The second light transmission element F2 is arranged as part of a wall of the flow channel in the device for determining the concentration of a gas component such that a distance $l_{F2}$ is obtained for the second light transmission element F2 in relation to the vertical distance $l_3$ according to the following relationship:

$$\frac{l_{F2}}{l_3} \geq 0.5,$$

and a distance $l_{F2}$ is obtained for the second light transmission element F2 in relation to the vertical distance $l_3$ and ratios according to the following relationship:

$$0 \leq \frac{l_{DB}}{l_3} \leq \frac{l_{F2}}{l_3}$$

are obtained in relation to the distance $l_{DB}$ from the detection surfaces of the two detector arrays.

The first light transmission element F1 is arranged in the device for determining the concentration of a gas component as part of a wall of the flow channel such that a distance $l_{F1}$ is obtained for the first light transmission element F1 in relation to the vertical distance $l_3$ according to the following relationship:

$$\frac{l_{F1}}{l_3} \leq 0.3.$$

The diaphragm element B is arranged in the device for determining the concentration of a gas component at or outside the flow channel such that a ratio according to the following relationship:

$$\frac{l_B}{l_S} \geq 0.25$$

is obtained for the horizontal extension of the diaphragm element B in relation to a horizontal (width direction) extension $l_S$ of the radiation source.

The diaphragm element B in the device for determining the concentration of a gas component is arranged at or outside the flow channel such that a ratio according to the following relationship:

$$\frac{l_B}{l_S} \geq \frac{l_{D1,2}}{l_S}$$

is obtained for the horizontal extension of the diaphragm element B in relation to a horizontal extension $l_S$ of the radiation source (30) and to horizontal extensions of the detector arrays $l_{D1,2}$.

These geometric relationships lead to the formation of a range of overlap for the light emission generated by the radiation source between the two detector arrays in the flow channel in the first embodiment of the device for determining the concentration of a gas component. These relationships as ratios of lengths and distances are obtained according to the first embodiment from the lengths and distance definitions according to Tables 2a and 2b.

According to the second embodiment of the present invention, a compact arrangement of the device for determining the concentration of a gas component is obtained with a radiation source suitable and configured for emitting a light emission in wavelength range of lambda1 ($\lambda 1$)=2.5 µm to lambda2 ($\lambda 2$)=14.0 µm, with an optically reflecting element, which is suitable for light reflection and is arranged opposite the radiation source, with two detector arrays, with two detector elements configured suitably for detecting radiation reflected by the optically reflecting element, with two bandpass filter elements, which are arranged at the two detector elements and which form detection surfaces for detecting the light emission generated by the radiation source, with a flow channel, which is configured for guiding the flow of a gas flow essentially at right angles to a vertical (length) axis of the light emission, with a first light transmission element F1 and with second light transmission element F2, which are both configured as being optically transparent for the light emission in the wavelength range of lambda1 ($\lambda 1$)=2.5 µm to lambda2 ($\lambda 2$)=14.0 µm, with a diaphragm element B for guiding a light beam from the radiation source to the detection surfaces of the two detector arrays, and with a control unit for controlling the operation of the radiation source and for detecting the signals of the two detector elements.

One of the two bandpass filter elements is configured as being optically transparent for an infrared radiation that is absorbed by a measured gas, and one of the two bandpass filter elements for an infrared radiation is configured as being optically transparent for a radiation that is not absorbed by the measured gas.

A reflection surface of the optically reflecting element is arranged at a vertical distance $l_3$ from the two detection surfaces of the two detector arrays.

The second light transmission element F2 is arranged as part of a wall of the flow channel in the device for determining the concentration of a gas component such that a distance $l_{F2}$ is obtained for the second light transmission element F2 in relation to the vertical distance $l_3$ according to the following relationship:

$$\frac{l_{F2}}{l_3} \geq 0.5$$

and a distance $l_{DB}$ is obtained in relation to the detection surfaces of the two detector arrays for the second light transmission element F2 and ratios according to the relationship:

$$0 \leq \frac{l_{DB}}{l_3} \leq \frac{l_{F2}}{l_3}$$

are obtained in relation to the distance $l_{DB}$ from the detection surfaces of the two detector arrays.

The first light transmission element F1 is arranged as part of a wall of the flow channel in the device for determining the concentration of a gas component such that a distance $l_{F1}$ is obtained in relation to the vertical distance $l_3$ for the first light transmission element F1 according to the following relationship:

$$\frac{l_{F1}}{l_3} \leq 0.3.$$

The diaphragm element B is arranged at or outside the flow channel in the device for determining the concentration of a gas component such that a ratio according to the following relationship:

$$\frac{l_B}{l_R} \geq 0.25$$

is obtained for the horizontal (width) extension of the diaphragm element B in relation to a horizontal extension $l_R$ of the optically reflecting element.

The diaphragm element B is arranged at or outside the flow channel in the device for determining the concentration of a gas component such that a ratio according to the following relationship:

$$\frac{l_B}{l_R} \geq \frac{l_{D1,2}}{l_R}$$

is obtained for the horizontal extension of the diaphragm element B in relation to a horizontal extension $l_S$ of the radiation source and to horizontal extensions of the detector arrays $l_{D1,2}$.

These geometric relationships lead to the formation of a range of overlap between the two detector arrays for the radiation reflected by the optically reflecting element in the flow channel in the second embodiment of the device for determining the concentration of a gas component. These relationships as ratios of lengths and distances are obtained according to the second embodiment from the length and distance definitions according to Tables 2a and 2b.

The above-mentioned relationships for geometric structural configurations, which lead to the compact configuration with range of overlap in the flow channel according to the first embodiment as well as the second embodiment, are listed synoptically once again in Table 3.

TABLE 3

|   | First embodiment Relationships (equations, formulas) |   | Second embodiment Relationships (equations, formulas) |
|---|---|---|---|
| A | $\frac{l_{F2}}{l_3} \geq 0.5$ | A | $\frac{l_{F2}}{l_3} \geq 0.5$ |
| B | $0 \leq \frac{l_{DB}}{l_3} \leq \frac{l_{F2}}{l_3}$ | B | $0 \leq \frac{l_{DB}}{l_3} \leq \frac{l_{F1}}{l_3}$ |
| C | $\frac{l_{F1}}{l_3} \leq 0.3$ | C | $\frac{l_{F1}}{l_3} \leq 0.3$ |
| D | $\frac{l_B}{l_S} \geq 0.25$ | D' | $\frac{l_B}{l_R} \geq 0.25$ |
| E | $\frac{l_B}{l_S} \geq \frac{l_{D1,2}}{l_S}$ | E' | $\frac{l_B}{l_R} \geq \frac{l_{D1,2}}{l_R}$ |

In a preferred configuration of the first embodiment, the radiation source is configured as a flat radiator, as a diaphragm radiator or as a radiation element configured with an essentially planarly configured radiation element or as a light-emitting diode (LED) configured with an essentially planarly configured radiating surface. The radiating surface is configured for uniform radiation over the radiating surface. The radiating surface of the flat radiator or of the diaphragm radiator as well as the radiating surface of an essentially planarly configured light radiating surface of the light-emitting diode are preferably configured for a device according to the first embodiment according to the present invention in a range of 2.0 mm² to 10 mm². The distance $l_0$ between the two detector arrays is in a range of 0.05 mm to 1.0 mm.

In a preferred configuration of the second embodiment, the radiation source is configured as a spotlight or as a light-emitting diode (LED) radiating in a punctiform manner (a punctiform shape) with a radiating surface directed essentially with a horizontal radiation angle of 80° to 170° in the direction of the reflecting element and for uniform radiation in the direction of the optically reflecting element. The radiating surface of the spotlight as well the radiating surface of the light-emitting diode radiating in a punctiform manner are preferably configured for a device having the configuration according to the present invention in a range of about 0.05 mm² to 1.0 mm². The distance $l_0$ between the two detector arrays is in a range of about 200 μm to 800 μm. The reflection surface of the optically reflecting element located opposite the radiation source is preferably configured for a device according to the second embodiment according to the present invention in a range of 2.0 mm² to 10 mm².

In a preferred configuration of the second embodiment, the optically reflecting element is provided with a surface structure which is configured for a preferably uniform distribution, for example, by means of light mixing or light scattering of the reflected light between the two detector arrays. Such a surface structure is, for example, a pattern with grooves, depressions, engravings or recesses, which may be formed by means of shaping by hollowing or embossing in plastic material. An alternative to this is represented by a film structured with a surface structure, which is applied to the optically reflecting element.

Each of the two detector elements is preferably arranged, according to the first and second embodiments, at a first distance $l_1$ from a vertical (length) axis extending preferably centrally between the two detector elements in a range of 0.1 mm to 10 mm.

Each of the two bandpass filter elements arranged at the two detector elements is preferably arranged, according to the first and second embodiments, at a second distance $l_2$ from the vertical axis extending preferably centrally between the two detector elements in a range of 0.1 mm to 10 mm.

In another preferred embodiment, the detector elements are configured as thermopiles or thermocouples.

In another preferred embodiment, the detector elements are configured as semiconductor detectors, for example, InAsSb detectors (indium-arsenic-antimony detectors).

In another preferred embodiment, the detector elements are configured as pyrodetectors.

In another embodiment, the detector elements are configured as bolometers.

The advantages that can be mentioned for thermocouples, thermopiles, pyrodetectors and bolometers are that these can be manufactured at a favorable cost and can be used as heat detectors in a broad wavelength range of 3 μm to 14 μm.

The fact that the measuring sensitivity of semiconductor detectors can be adapted very well to the desired wavelength range can be mentioned as an advantage of semiconductor detectors. In addition, semiconductor detectors have shorter signal rise times ($t_{10\_90}$).

In a preferred embodiment, the first light transmission element and the second light transmission element form the flow channel suitable for guiding inhaled gas and/or exhaled gas in the device for determining the concentration of least one gas component in breathing gas mixture according to the first embodiment as well as according to the second embodiment. The inhaled gas and/or exhaled gas is sent through the flow channel as a main stream and it passes in the process through the beam path between the radiation source and the two detector elements and the bandpass filter elements arranged thereon. The gas concentration is detected in the main stream. The device for determining the concentration of at least one gas component in a breathing gas mixture is formed here according to the first embodiment by the detector arrays, the first light transmission element and the second light transmission element, the diaphragm element and the radiation source. The device for determining the concentration of at least one gas component in a breathing gas mixture is formed here according to the second embodiment by the detector arrays, the first light transmission eminent and the second light transmission element, the diaphragm element, the optically reflecting element and the radiation source.

A configuration of such an embodiment is, for example, a device for carbon dioxide measurement in the exhaled gas of a patient as a device located directly at the area of the patient's mouth, which is often also called a so-called "mainstream $CO_2$ sensor."

Another configuration of such an embodiment is, for example, an analysis unit for measuring carbon dioxide and other gas concentrations, especially anesthetic gases, at patients, in which unit a quantity of gas is suctioned or delivered continuously to the analysis unit from the area of the mouth directly at the mouth by a pump arranged in the analysis unit via a tube of a small diameter and the quantity of gas is analyzed there in respect to the composition of the gas and the gas concentration. Both the inspiratory and the expiratory patient gas concentrations are of interest here. Such a measurement method is often also called "suctioning gas measurement" or so-called "sidestream anesthetic gas monitoring."

The overall size of the device for determining the concentration of at least one gas component in a breathing gas mixture plays a rather important role for applications of gas measurements in the field of anesthesia, especially for the "sidestream" application. In conjunction with the overall sizes of the radiation source with a radiating surface in the preferred range of 2.0 mm² to 10.0 mm² of the detector elements (bolometer, microbolometer, microbolometer arrays, pyrodetectors, thermocouples, thermopiles, semiconductor detectors) and bandpass filter elements with detector surfaces in a preferred range of 0.5 mm² to 20 mm² and with the arrangement of the two detector elements in relation to one another at distances in a preferred range smaller than 10 mm, the distance $l_3$ in a preferred range of 0.1 mm to 10 mm between the radiation source and the detector elements and bandpass filter elements as well as the distance $l_{3'}$ in the range of 0.1 mm to 5.0 mm between the radiation source and the optically reflecting element (mirror, reflector) make it possible to obtain an overall size for the device for determining the concentration of at least one gas component in a breathing gas mixture with a small measurement volume in a range of less than 0.4 mL, for example, 0.05 mL to 0.2 mL.

In case of "suctioning gas measurement" with a suction volume flow of 50 mL/min to 200 mL/min with the pump arranged in the device, the duration for the exchange of the measured volume in the device for determining the concentration of at least one gas component in a breathing gas mixture will be 0.1 sec to 0.5 sec.

Compared to respiration rates of humans in the range of about 6 breaths per minute to 24 breaths per minute (corresponding to 0.1 to 0.4 breaths per second), the device for determining the concentration of at least one gas component in a breathing gas mixture, which is provided by this invention, makes possible a measuring time resolution that makes it possible, in conjunction with a fittingly selected scanning rate, to detect concentration changes in the breathing gas as measured data resolved for individual breaths.

The overall size generally plays another important role, because not only is a small measurement volume made possible due to the distances, but the optical path lengths between the detector elements and the radiation source must be kept short as well. This makes it possible for measured data that have a sufficient signal height with a good signal-to-noise ratio (SNR) to be detectable at the detector elements, so that a high measuring sensitivity with robust signal quality is available, which make possible a largely noise-free, high measuring resolution, e.g., with a 16-bit quantification or finer (20 bits, 24 bits) in conjunction with fitting amplifier circuits and high-quality analog-to-digital converters (A/D converters).

Another possibility of minimizing the overall size and the geometric structural configuration is given in another preferred embodiment due to space areas, which space areas are provided between: the detector array and the diaphragm element B, the diaphragm element B and the second light transmission element F2, the radiation source and the first light transmission element F1, the optically reflecting element and the first light transmission element F1 and the detector array and the light transmission element F2. The space areas may be filled with an optically transparent material, for example, a plastic material, quartz, germanium or silicon, which has an optical refractive index n≥1. This leads to possibilities of reducing the distances $l_3, l_{F1}, l_{F2}, l_{DB}$ mentioned in Table 1 by the refractive index n of the material being used as a factor.

In another preferred embodiment, this leads to the possibility of using the lengths $l_3, l_{F1}, l_{F2}, l_{DB}$ mentioned in Table 1 as physical optical length extensions instead of as physical geometric length extensions, using the optical refractive indices n of the optically transparent materials, which fill the space area, for the geometric configuration of the device for determining the concentration of at least one gas component in a breathing gas mixture as a compact arrangement. The dimensioning of the lengths $l_{F1}, l_{F2}, l_{DB}$, in which the optically transparent materials are introduced in a space-filling manner, now decreases by a factor that corresponds to the numerical value of the optical refractive index n. As a result, the possibility of reducing the distance $L_{F2}$ between the detector array and the second light transmission element F2 leads, taking the relationship:

$$\frac{l_{F2}}{l_3} \geq 0.5$$

(A, Table 3) into account, to the possibility of reducing the vertical distance $l_3$ between the radiating surface of the radiation source and the two detection surfaces of the two detector arrays or between the reflection surface of the optically reflecting element and the two detector surfaces of the two detector arrays.

The fact that no gas can penetrate from the flow channel into components, into the beam path or into areas of the radiation and/or reflected radiation in the device for determining the concentration of at least one gas component in a breathing gas mixture arises as another advantage that is obtained with the filling of the space areas between the detector array and the diaphragm element B, the diaphragm element B and the second light transmission element F2, the radiation source and the first light transmission element F1, the optically reflecting element and the first light transmission element F1 or the detector array and the second light transmission element F2. The penetration of gases into these space areas is prevented by this filling, even if leaks should develop in the sealing of the light transmission elements in the flow channel in the course of the operation of the device for determining the concentration. The penetration and a long-term presence of, for example, carbon dioxide, for example, in the space area between the detector array and the first light transmission element F1, would be able to distort the measurements in the further course of the $CO_2$ measurement during the further course of operation, because these penetrated quantities of $CO_2$ would bring about an additional wavelength-specific attenuation in the beam path. This problem can be abated by filling the space areas with optically transparent material.

Due to the overlap of the measuring channel and the reference channel, it is advantageously achieved that the measured data, which are resolved for individual breaths and are detected for effects that affect both the measuring channel and the reference channel in a similar manner, for example, changes in the temperature of the measured gas, impurities, water vapor, moisture, contaminations of the radiation source or of the optically reflecting element, are available directly and without undue delay at the time of the actual physical measurement without major effort for further signal processing and correction of measured data, for example, moisture and/or temperature compensation, on the basis of externally provided moisture and/or temperature data.

The embodiments described represent, both in themselves and in combination or combinations with one another, special embodiments of the device for determining the concentration of gas components in a breathing gas mixture. All embodiments and possible additional embodiments arising through combinations or combinations of a plurality of embodiments and their advantages are also equally covered by the inventive idea, even though not all possibilities of combinations of embodiments are described specifically in detail for this.

The present invention will be explained in more detail below by means of the following figures and the corresponding descriptions of the figures without limitations of the general inventive idea.

The present invention will be described in detail below with reference to the figures attached. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1A:
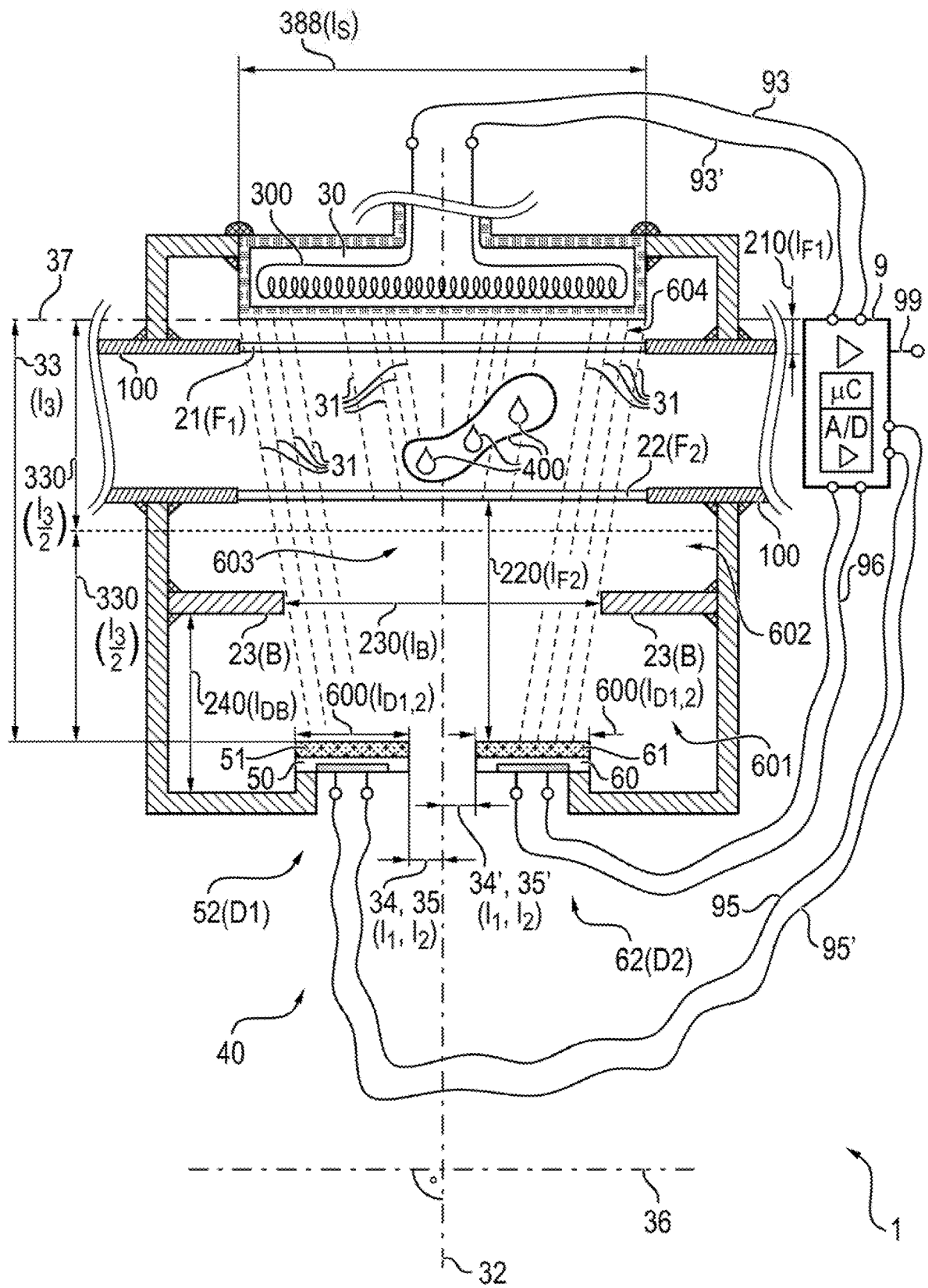
FIG. 1a is a first schematic view of a device for concentration determination.

Referring to the drawings, FIG. 1a shows a first schematic view of a device 1 for determining the concentration of at least one gas component in a breathing gas mixture. The device 1 shown has a radiation source 30 with a radiation element 300. A detector element 50 and a detector element 60 are arranged opposite the radiation source 30 at a vertical (length) distance $l_3$ 33. Bandpass filter elements 51, 61 are arranged at the detector elements 50, 60. The bandpass filter elements 51, 61 are preferably configured as bypass filter elements that are transparent to a predefined wavelength range of the radiation 31 emitted by the radiation source 30. This FIG. 1a shows a coordinate system with vertical (length) reference axis 32 and with a horizontal (width) reference axis 36, to which system reference is made in the description of the positions of the components in relation to one another. Thus, a radiation takes place from the radiation source 30 out of a horizontal plane of radiation 37, the horizontal plane 37 being parallel to the horizontal reference plane 36. A control unit 9 is provided, which is connected to the radiation element 300 by means of control lines 93, 93'. Furthermore, the control unit 9 is connected to the detector element 60 by means of control lines 96, 96'. The control unit 9 is furthermore connected to the detector element 50 by means of control lines 95, 95'. The detector element 50 together with the corresponding filter element 51 forms a detector array 52. The detector element 60 together with the corresponding filter element 61 forms a detector array 62. The detector arrays 52 and 62 together form a detector configuration 40, which functionally forms the device 1 for determining the concentration of a gas component in conjunction with the radiation source 30 and the control unit 9. The arrangement of the detector configuration 40 in relation to the vertical axis 32 and to the horizontal reference axis 36 is determined by distances of the detector arrays 52, 62. The detector array 52 is configured in this FIG. 1a in a parallel arrangement to the horizontal reference axis 36 as well as to the horizontal plane of the radiation 37. A horizontal (width) distance $l_1$ 34 of the detector element 50 to the central axis 32 is obtained in the detector configuration 40. A distance $l_1$ 34' is obtained for the detector element 60 from the central axis 32 in the detector configuration 40. A distance $l_2$ 35 of the bandpass filter element 51 is obtained from the central axis 32 in the detector configuration 40. Furthermore, a distance $l_2$ 35' is obtained for the filter element 61 from the central axis 32 in the detector configuration 40. Due to the detector arrays 52, 62 being arranged at right angles in relation to the central axis 32, the distances $l_1$ 34 and $l_2$ 35 between the central axis 32 and the detector element 50, on the one hand, and the filter element 51, on the other hand, are identical.

A flow channel 100, which is arranged between the radiation source 30 and the detector arrays 52, 62 in parallel to the horizontal reference axis 36, is shown in the schematic view of the device 1 for determining the concentration of at least one gas component in a breathing gas mixture. A first transparent light transmission element F1 21 and a second transparent light transmission element F2 22 are arranged opposite each other in walls of the flow channel 100, whereby a radiation 31 is made possible from the radiation source 30 through the flow channel 100.

Extensions or expansions of the components as well as distances of the components in relation to one another are shown in this FIG. 1a in the form of lengths, as they are listed in Tables 2a and 2b.

A distance $l_{F1}$ 210 between the light transmission element F1 21 and the radiation source 30 is shown.

A distance $l_{F2}$ 220 between the light transmission element F2 22 and the detector arrays 52, 62 is shown.

A distance $l_{DB}$ 240 between the diaphragm element B 23 and the detector arrays 52, 62 is shown.

The vertical distance $l_3$ 33 between the radiation source 30 and the detector arrays 52, 62 is shown.

A horizontal extension $l_S$ 388 of the radiation source 30 is shown.

A horizontal extension $l_B$ 230 of an aperture of the diaphragm B 23 is shown.

Horizontal extensions lD1,2 600 of the detector arrays 52, 62 are shown.

The device 1 for determining the concentration of at least one gas component in a breathing gas mixture according to this FIG. 1a is structurally configured such that using the relationships A, B, C, D, E according to Table 3 as the basis for the structural dimensioning, a configuration of a compact arrangement with a range of overlap 65 (FIG. 4) is obtained.

Due to this configuration of the compact arrangement, which is obtained on the basis of the application of the geometric structural conditions shown above by means of the relationships A, B, C, D, E listed above in Table 3 for the first embodiment and on the basis of a distance $l_0$ 38 (FIG. 4) between the two detector arrays 52, 62 in the detector configuration 40, as well as of the distances 34, 34', 35, 35' from the vertical central axis 32 of the horizontal extension $l_S$ 388 of the radiation source 30, of the horizontal extension $l_B$ 230 of the aperture of the diaphragm B 23, and of the horizontal extensions lD1,2 600 of the detector arrays 52, 62 in conjunction with the vertical distance $l_3$ 33, the range of overlap 65 (FIG. 4) in the radiation 31 emitted by the radiation source 30 is obtained for the radiation 31 emitted by the radiation source 30 along the vertical distance between the radiation source 30 and the detector configuration 40.

This range of overlap 65 (FIG. 4) is obtained vertically from the plane of the detector arrays 52, 62 in the direction of the radiation source 30. Due to this, the situation is obtained, for example, for gas molecules or condensate (moisture, such as water vapor or water droplets) 400, which are shown in this FIG. 1a, for example, on the central axis 32 in the vicinity of the radiation source 30, in which the radiation 31 of radiation source 30 passes through this gas molecule 400 and it becomes effective as radiation 31 onto both the detector element 50 and onto the detector element 60. It is thus ensured that, for example, moisture (condensate) 400 attenuates the radiation onto both the detector element 50 and onto the detector element 60 in the same manner. This leads to the possibility of eliminating the influence of moisture and impurities from the formation of the ratio of the signals of the detector element 50 and of the detector element 60.

Reference should be made in this description of FIG. 1a to FIG. 4, in which the effects are schematically illustrated in the construction of the device 1 according to the described conditions A, B, C, D, E concerning the range of overlap 65 (FIG. 4) in the radiation 31 in a simplified, graphic form.

The control unit 9 analyzes the signals of the detector elements 50, 60 by means of suitable electronic components (amplifier, analog-to-digital converter, microcontroller) and provides an output signal 99. The output signal 99 is representative here of the signals detected by the detector elements 50, 60 as well as of the ratio of the detected signals and it is also representative of a gas concentration derived from these signals or signal ratio.

Figure 1B:
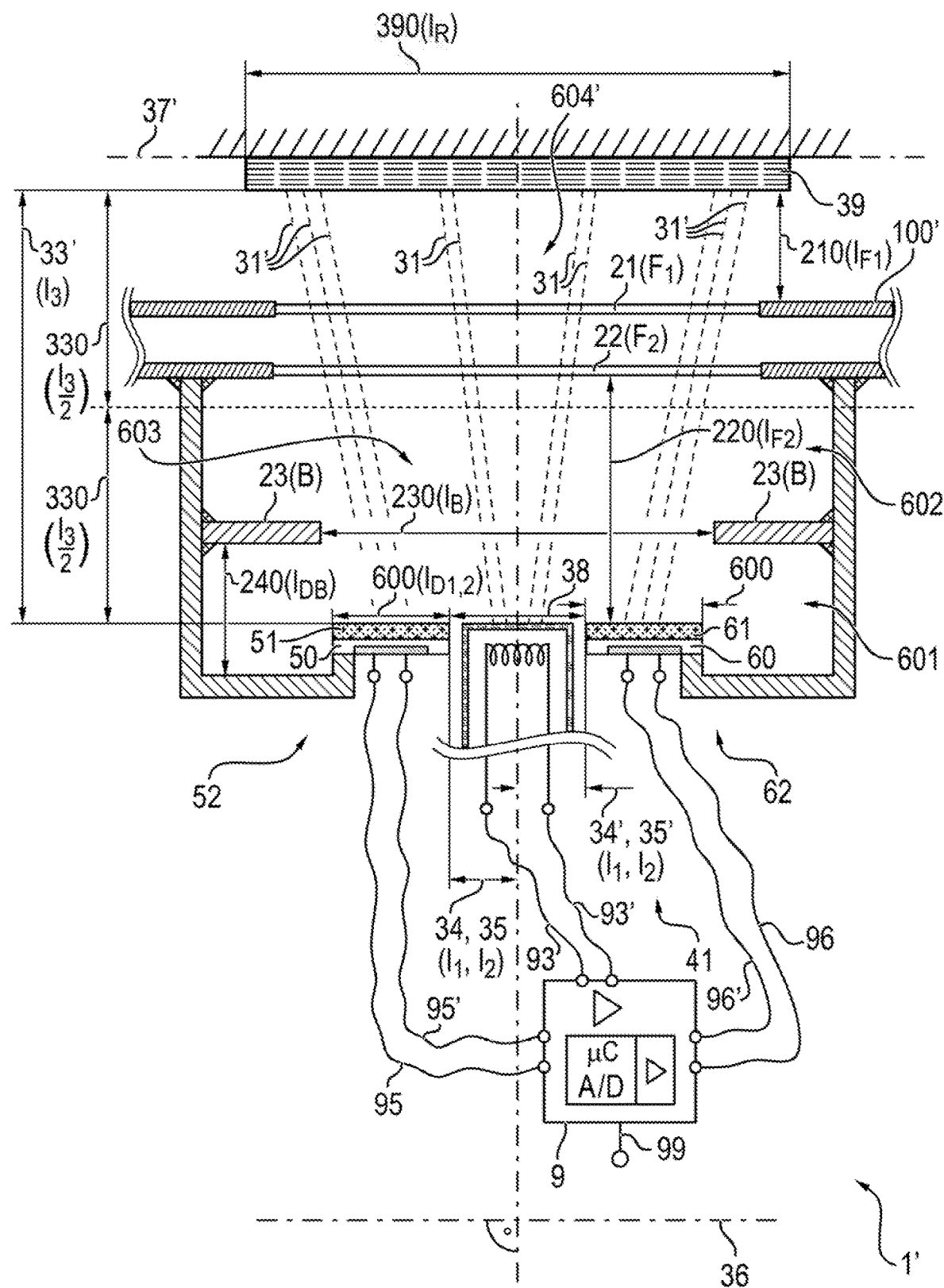
FIG. 1b is another, second schematic view of a device for concentration determination.

FIG. 1b shows another, second schematic view of a device 1' for determining the concentration of at least one gas component in a breathing gas mixture. Components that are identical in FIG. 1a and in FIG. 1b are designated by the same reference numbers as are the correspondingly equivalent components in FIG. 1a.

FIG. 1b shows with the additional, second schematic view a modified variant of FIG. 1a. Unlike in FIG. 1a, the radiation source 30 is arranged in FIG. 1b on the same side as the optical elements and the detectors. The device 1' shown has a radiation source 30 (the numbering is missing in FIG. 1b) with a radiation element 300. A detector element 50 and an additional detector element 60 are arranged directly adjacent to the radiation source 30. Bandpass filter elements 51, 61 are arranged at the detector elements 50, 60. A reflector 39, for example, a mirror or plane mirror, is arranged as an optically reflecting element opposite the radiation source 30. The reflector 31 acts as a mirror for the radiation 31 emitted by the radiation source 30 and brings about a reflection of a reflected radiation 31' towards the bandpass filter elements 51, 61 as well as towards the detector elements 50, 60. The bandpass filter elements 51, 61 are transparent to light in a predefined wavelength range. A coordinate system with vertical reference axes 32 and horizontal reference axes 36 is shown in this FIG. 1b. These axes are used, similarly to their use described in the description of FIG. 1a, as a reference for the position of the components in relation to one another and in space. A control unit 9 is provided, which is connected to the radiation element 300 of the radiation source 30. The arrangement by means of control line 93, 93' and 96, 96' as well as 95, 95' for connecting the control unit 9 to the detector elements 60, 50 corresponds to the arrangement according to FIG. 1a and to the corresponding description, which shall then be used as a reference for this. The detector element 50 forms a detector array 52 together with the corresponding filter element 51. The detector element 60 likewise forms a detector array 62 together with the corresponding filter element 61. These detector arrays 52, 62 form, together with the radiation source 30, a detector configuration 41, which functionally form the device 1' for determining the concentration of a gas component in conjunction with the control unit 9 and the reflector 39. The arrangement of the detector configuration 41 in reference to the axes 32, 36 is determined by distances of the detector arrays 52, 62. The detector arrays 52, 62 are each configured in this FIG. 1b at right angles to the vertical central axis 32. A horizontal distance $l_1$ 34 is obtained between the detector element 50 and the central axis 32 in the detector configuration 41. A distance $l_1$ 34' is obtained in the detector configuration 41 for the detector element 60 from the central axis 32. A distance $l_2$ 35 is obtained between the bandpass filter element 51 and the central axis 32 in the detector configuration 41. Due to the detector arrays 52, 62 being arranged at right angles to the central axis 32, the distances $l_1$ 34' and $l_2$ 35' from the central axis 32 are identical for the detector element 50 and the filter element 51. Furthermore, a distance $l_2$ 35' is obtained in the detector configuration 41 between the filter element 61 and the central axis 32. Due to the detector arrays 52, 62 being arranged at right angles to the central axis 32, the distances $l_1$ 34 and $l_2$ 35 of the detector element 50 and the filter element 51 from the central axis 32 are identical.

A flow channel 100', which is arranged between the reflector 39 and the detector arrays 52, 62 parallel to the horizontal reference axis 36, is shown in the schematic view of the device 1' for determining the concentration of at least one gas component in a breathing gas mixture. A first transparent light transmission element F1 21 and a second transparent light transmission element F2 22 are arranged opposite each other in walls of the flow channel 100', as a result of which a radiation 31 is made possible by means of the radiation source 30 and by means of the reflector 39 of reflected radiation 31' through the flow channel 100'.

Extensions or expansions of the components as well as distances between the components are shown in this FIG. 1b in the form of lengths, as they are listed in Tables 2a and 2b.

A distance $l_{F1}$ 210 between the light transmission element F1 21 and the reflector 39 is shown.

A distance $l_{F2}$ 220 between the light transmission element F2 22 and the detector arrays 52, 62 is shown.

A distance $l_{DB}$ 240 between the diaphragm element B 23 and the detector arrays 52, 62 is shown.

A vertical (length) distance $l_3$ 33' between the reflector 39 and the detector arrays 52, 62 is shown.

A horizontal (width) extension lR 390 of the reflector 39 is shown.

A horizontal (width) extension $l_B$ 230 of an aperture of the diaphragm B 23 is shown.

Horizontal (width) extensions lD1,2 600 of the detector arrays 52, 62 are shown.

The device 1' for determining the concentration of at least one gas component in a breathing gas mixture according to FIG. 1b is structurally configured such that using the relationships A, B, C, D', E' according to Table 3 as the basis of the structural dimensioning, a configuration of a compact arrangement with a range of overlap 65 (FIG. 4) is obtained.

In conjunction with the vertical distance $l_3$ 33', the range of overlap 65 (FIG. 4) is obtained for the radiation 31' reflected from the reflector 39 along the vertical distance between the radiation source 30 and the detector configuration 41 due to the configuration of the compact arrangement, which is obtained on the basis of the application of the geometric structural conditions shown above by means of the relationships A, B, C, D', E' listed in Table 3 for the second embodiment and on the basis of a distance $l_0$ 38 (FIG. 4) between the two detector arrays 52, 62 in the detector configuration 41 as well as of the distances 34, 34', 35, 35' to the vertical central axis 32, of the horizontal extension $l_R$ 390 of the reflector 39, of the horizontal extension $l_B$ 230 of the aperture of the diaphragm B 23, and of the horizontal extensions lD1,2 600 of the detector arrays 52, 62. This range of overlap 65 (FIG. 4) is obtained vertically from the plane of the detector arrays 52, 62 in the direction of the radiation source 30. The detector arrays 52, 62 are configured in reference to the horizontal reference axis 36, the central axis 32 and to a horizontal plane of the light reflection of the reflector 37', which reflector is arranged parallel to the horizontal reference axis 36. The range of overlap 65 (FIG. 4), which is obtained on the basis of the detector arrays 52 and 62, causes impurities or condensate, which are present in the reflected radiation 31, for example, in the vicinity of the reflector 39, to influence, i.e., possibly attenuate the radiation to the detector element 50 as well as to the detector element 60 in the same manner. As is described in connection with FIG. 4, this leads to the possibility of eliminating the influence of moisture 400 (FIG. 1a) or impurities from the ratio of the signals of the detector element 50 and of the detector element 60.

Figure 4:
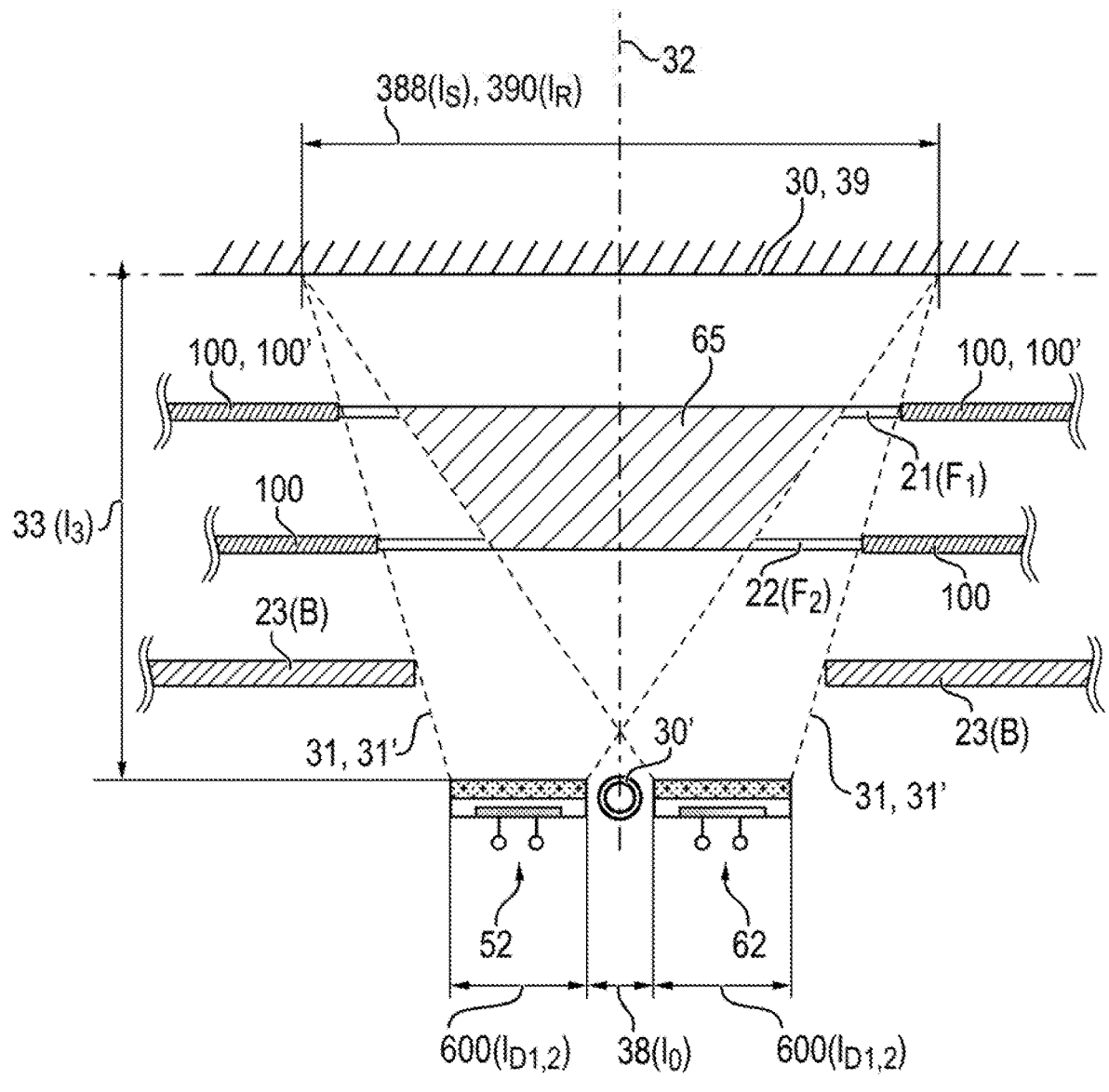
FIG. 4 is a view of the range of overlap in a device for concentration determination according to FIGS. 1a and 1b.

Reference should be made in this description to FIG. 1b and FIG. 4, in which the effects are schematically illustrated in the construction of the device 1' according to the described conditions A, B, C, D', E' concerning the range of overlap 65 (FIG. 4) in the reflected radiation 31' in a simplified graphic form.

Contrary to FIG. 1a, a longer beam path, in the simplest case a doubled beam path is obtained in this FIG. 1b for the path of the radiation 31 towards the reflector 39 and for the path of the reflected radiation 31' to the detector elements 50, 60. The consequence of this is that the light beams reaching the detector elements 50, 60 have a lower intensity than in FIG. 1a. This leads to a difference concerning the sensitivity of the device 1' for determining the concentration of a gas component in this FIG. 1b. The analysis of the signals of the detector elements 50, 60 in the control unit 9 takes place by means of suitable electronic components similarly to how it is described in connection with FIG. 1a. The control unit provides an output signal 99, which is representative of the signals of the detector elements 50, 60 or of the ratio of the signals of the detector elements 50, 60. Thus, the output signal 99 provides a gas component derived from the signals on the basis of the detected signals of the detector elements 50, 60 for further processing, for example, in a display unit 94 (FIG. 2).

Figure 2:
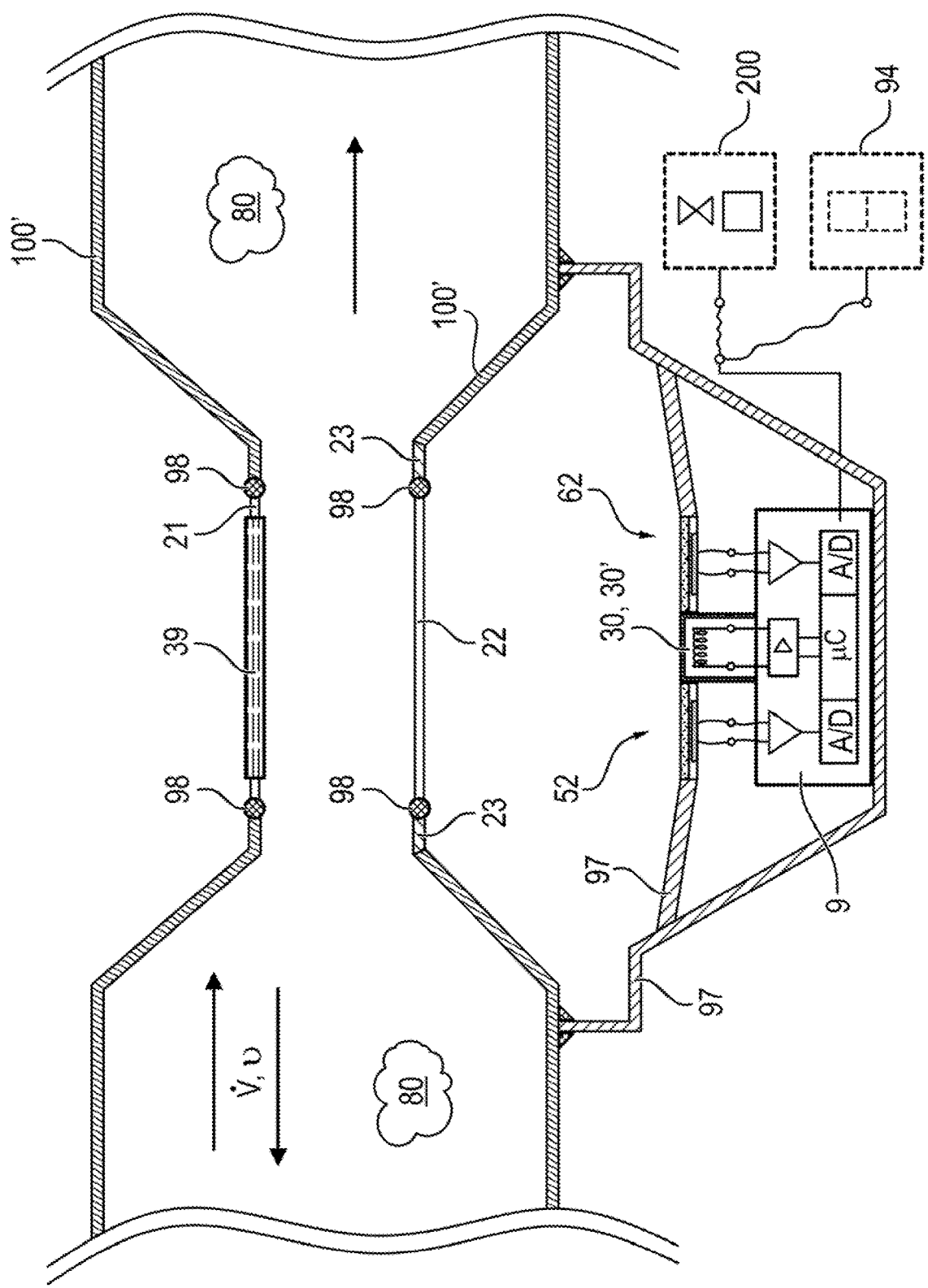
FIG. 2 is an arrangement of a device for concentration determination at a flow channel.
Figure 3:
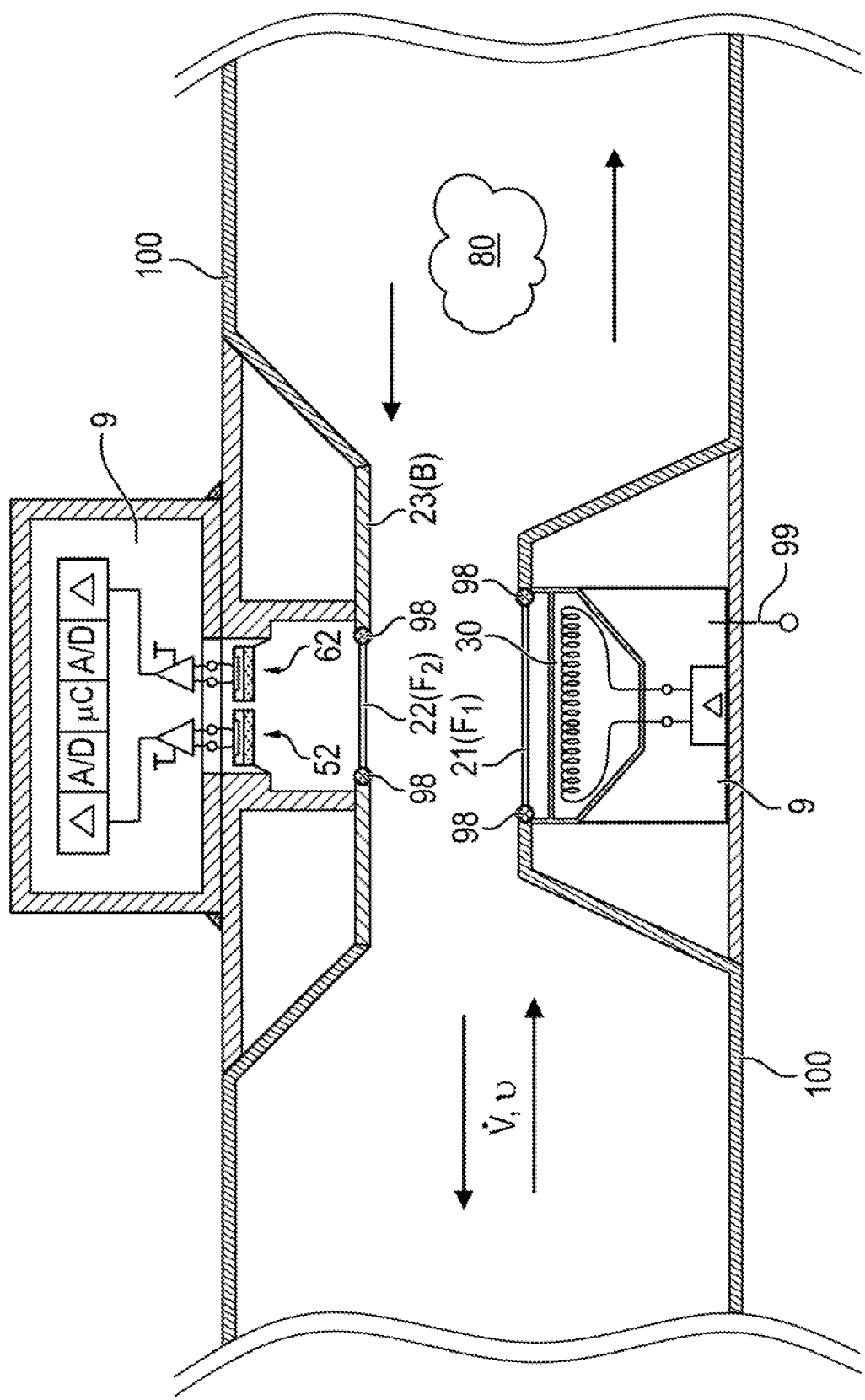
FIG. 3 is another arrangement of a device for concentration determination at a flow channel.

FIGS. 2 and 3 show arrangements of a device for determining the concentration according to FIGS. 1a, 1b. FIGS. 2, 3 shall be described in a joint description of the figures concerning the common feature they share, but also concerning the differences from one another. Identical components in FIGS. 2, 3 are designated by the same reference numbers as the correspondingly identical components in FIGS. 2, 3. Identical components in FIGS. 2, 3 and in FIGS. 1a, 1b are designated by the same reference numbers as the correspondingly identical components in FIGS. 2, 3 as well as in FIGS. 1a, 1b.

FIG. 2 shows device 1 for determining the concentration of a gas component (FIG. 1b). The flow channel 100' is configured to feed a flow with a quantity of gas 80 for measurement by means of the device 1' (FIG. 1b). Detector arrays 52, 62 are shown in conjunction with a radiation source 30, with a radiation element 300 configured as a spotlight 30' and with a control unit 9. The detector arrays 52, 62 with the radiation source 30 and with the control unit 9 are arranged in a holding element 97, which is coupled with the flow channel 100'. The flow channel 100' has a first light transmission element F1 21, which forms an assembly unit with a reflector 39 in a wall of the flow channel 100'. The flow channel 100' has a second light transmission element F2 22, which forms an assembly unit with a diaphragm element 23 in a wall of the flow channel 100'. The light transmission elements F1 21, F2 22 are configured for passing through light that is emitted by the radiation source 30, 30' and for passing through light reflected by the reflector 39. The light transmission elements F1 21, F2 22 as well as the reflector 39 and the diaphragm element 23 are arranged on the flow channel 100' by means of sealing elements in order to guarantee the gas-tightness of the flow channel 100'. The mode of operation of the arrangement according to FIG. 2 is as described in connection with FIG. 1b.

Contrary to FIG. 2, FIG. 3 shows a device 1 for determining the concentration of a gas component according to FIG. 1a. The radiation source 30 is arranged opposite two detector arrays 52, 62 at the flow channel 100. The detector arrays 52, 62 with the radiation source 30 and with the control unit 9 are arranged in a holding element 97, which is coupled with the flow channel 100. The detector arrays 52, 62 and the radiation source 30 are arranged opposite each other at a location of the flow channel 100, at which the flow cross section is reduced in the form of a Venturi tube.

The flow channel 100 has a first light transmission element F1 21, which is arranged in a wall of the flow channel 100. The flow channel 100 has a second light transmission element F2 22, which forms an assembly unit with a diaphragm element 23 in a wall of the flow channel 100. The light transmission elements F1 21, F2 22 are configured for passing through light emitted by the radiation source 30. The light transmission elements F1 21, F2 22 as well as the diaphragm element 23 are arranged on the flow channel 100 by means of sealing elements 98 in order to guarantee the gas-tightness of the flow channel 100. It is necessary in this embodiment according to FIG. 3 to provide elements of a control unit 9 from two sides. This makes it possible to operate the detector arrays 52, 62 with the detector elements 50, 60 (FIG. 1a) and to amplify the signal. In addition, the control unit 9 is used to actuate the radiation source 30 and to output the output signal 99.

An output signal 99, which is representative, as was explained above in FIGS. 1a and 1b, of a detected gas concentration, is provided in FIGS. 2, 3.

FIG. 2 shows a medical device 200 as well as a display unit 94 in broken lines each as optional components. These optional components represent exemplary possibilities of sending the output signal 99 for further processing and use.

FIG. 3 does not show these optional components 200, 94, but they shall also be included in the embodiment according to this FIG. 3 based on the inventive idea.

FIG. 4 shows a view 1000 of the range of overlap 65 in devices 1, 1' for determining the concentration according to FIGS. 1a and 1b. Identical components in FIG. 4 and in FIGS. 1a, 1b, 2, 3 are designated in FIG. 4 by the same reference numbers as the correspondingly identical components in FIGS. 1a, 1b, 2, 3.

The effects are shown in the construction of the device 1 (FIG. 1a) as well as of the device 1' (FIG. 1b) when observing the conditions A, B, C, D, E or A, B, C, D', E' described in Table 3 concerning the range of overlap 65 in the radiation 31 according to FIG. 1a as well as in the reflected radiation 31 according to FIG. 1b. Two detector arrays 52, 62 are shown in a schematic form with a distance $l_0$ 38 between the two detector arrays 52, 62. An optically radiating element or an optically reflecting element configured as a radiation source 30 according to FIG. 1a or configured as a reflector 39 according to FIG. 1b is located opposite the detector arrays 52, 62.

A radiation source needed for a configuration according to FIG. 1b is positioned on a vertical axis 32 as a spotlight 30' between the two detector arrays 52, 62, comparably to what is shown in FIG. 1b.

It should be noted in this connection that this view according to FIG. 4 is a constellation with the radiation source 30, 30' and reflector 39 according to the device 1' (FIG. 1b), wherein the radiation source 30, 30' and the detector arrays 52, 62 are arranged adjacent to one another, while the constellation with the radiation source 30 according to device 1 (FIG. 1a), in which the radiation source 30 and the detector arrays 52, 62 are arranged opposite each other, does not require an optically reflecting element in the arrangement.

Since the effects on the construction conditions (distances, extensions, expansions) are comparable to the conditions A, B, C, D, E and A, B, C, D', E' described in Table 3 concerning the range of overlap 65, this is summarized and shown in this FIG. 4 in the view 1000. A flow channel 100, 100' with a first transparent light transmission element F1 21 and with a second transparent light transmission element F2 22 and with a diaphragm element 23, which are arranged in a wall of the flow channel 100, 100', is shown between the two detector arrays 52, 62 and the optically radiating element 30 or the optically reflecting element 39. The vertical arrangement of the first transparent light transmission element F1 21 and of the second transparent light transmission element F2 22, of the diaphragm element 23, of the detector arrays 52, 62 and of the optically radiating element 30 or of the optically reflecting element 39 is shown graphically in this FIG. 4 under conditions that arise from the application of the conditions A, B, C, D, E and A, B, C, D', E'. The range of overlap 65, which is obtained in the flow channel 100, 100' for radiation 31 from the radiation source 30 or for reflected radiation 31 to the two detector arrays 52, 62, can therefore be extrapolated concerning a relative extension of the range of overlap 65 in the flow channel 100, 100'. The greater the extension of the range of overlap 65 in the flow channel 100, 100', the more effectively is it possible to eliminate the influence of moisture and impurities by forming the ratio between the two detector elements 50, 60 (FIGS. 1a, 1b) of the first detector array and the second detector array 52, 62.

While specific embodiments of the invention have been shown and described in detail to illustrate the application of the principles of the invention, it will be understood that the invention may be embodied otherwise without departing from such principles.

APPENDIX

List of Reference Designations 1, 1' Device for determining the concentration of a gas component
9 Control unit
21 First light transmission element, window element (F1)
22 Second light transmission element, window element (F2)
23 Diaphragm element (B)
30 Radiation source
30' Radiation source 30 configured as a spotlight
31 Radiation
31' Reflected radiation
32 Vertical (length) axis, central axis, vertical reference axis, vertical axis
33 $l_3$, $l_3'$ vertical (length) distance
34 $l_1$ distance of the detector element 50 from the central axis 32
34' $l_1$ distance of the detector element 60 from the central axis 32
35 $l_2$ distance of the filter element 51 from the central axis 32
35' $l_2$ distance of the filter element 61 from the central axis 32
36 Horizontal (width) reference axis
37 Horizontal (width) plane of radiation
37' Horizontal (width) plane of light reflection
38 $l_0$ distance between the detector elements 50, 60
39 Optically reflecting element, reflector element Reflector, mirror element
40 Detector configuration
41 Detector configuration, reflective
50 Detector element
51 Bandpass filter element
52 Detector array
60 Detector element
61 Bandpass filter element
62 Detector array
65 Range of overlap
80 Quantity of gas, gas concentration
93, 93' Control line to the radiation element 300
94 Display unit
95, 95' Data line, signal line
96, 96' Data line, signal line
97 Holding element
98 Sealing elements
99 Output signal
100, 100' Flow channel
200 Medical device, ventilator, anesthesia apparatus
210 Distance $l_{F1}$ between light transmission element F1 and radiation source
220 Distance $l_{F2}$ between light transmission element F2 and detector array
230 Horizontal extension $l_B$ (width, length, diameter) of the diaphragm element (B)
240 Distance $l_{DB}$ between diaphragm element and detector array
300 Radiation element (diaphragm, coil)
388 Horizontal extension $l_S$ (width, length, diameter) of the radiation source
390 Horizontal extension $l_R$ (width, length, diameter) of the optically reflecting element, reflection element
400 Gas molecule, moisture, condensate
600 Respective horizontal extension lD1,2 (width, length, diameter) of the two detector elements
601 Space area between detector array and diaphragm element B
602 Space area between diaphragm element and second light transmission element F2
603 Space area between detector array and second light transmission element F2
604 Space area between first light transmission element F1 and radiation source
604' Space area between first light transmission element F1 and reflector element
1000 View of the range of overlap 65

What is claimed is:

1. A device for determining a concentration of a gas component in an inhaled gas or in an exhaled gas of a living being, the device comprising:
a radiation source configured to radiate light as a light emission in a wavelength range of lambda1 ($\lambda 1$)=2.5 µm to lambda2 ($\lambda 2$)=14.0 µm;
a first detector array comprising a first detector element configured to detect the light emission generated by the radiation source and a first array bandpass filter element arranged at the first detector element and which forms a detection surface for detecting the light emission generated by the radiation source;
a second detector array comprising a second detector element configured to detect the light emission generated by the radiation source and a second array bandpass filter element arranged at the second detector element and which forms a detection surface for detecting the light emission generated by the radiation source;
a flow channel configured to guide the flow of a gas flow essentially at right angles to a length axis of the light emission;
a first light transmission element;
a second light transmission element, each of the first light transmission element and the second light transmission element being configured to be optically transparent for the light emission in the wavelength range of lambda1 ($\lambda 1$)=2.5 µm to lambda2 ($\lambda 2$)=14.0 µm;
a diaphragm element configured to guide a light beam from the radiation source to the detection surfaces of the first detector array and the second detector array; and
a control unit configured to control operation of the radiation source and for detecting signals of the first detector element and the second detector element, wherein:
one of the first array bandpass filter element and the second array bandpass filter element is configured to be optically transparent for infrared radiation, which is absorbed by a measured gas, wherein another one of the first array bandpass filter element and the second array bandpass filter element is configured as being optically transparent for infrared radiation which is not absorbed by the measured gas;

a radiating surface of the radiation source is arranged at a radiation source distance ($l_3$) from the detection surface of the first detector array and the detection surface of the second detector array;

the second light transmission element is arranged as part of a wall of the flow channel;

a distance ($l_{F2}$) of the second light transmission element to the detection surfaces of the first detector array and the second detector array is related to the radiation source distance ($l_3$) according to a relationship:

$$\frac{l_{F2}}{l_3} \geq 0.5;$$

a diaphragm element distance ($l_{DB}$) from the detection surfaces of the first detector array and the second detector array to the diaphragm element is based on ratios according to a relationship:

$$0 \leq \frac{l_{DB}}{l_3} \leq \frac{l_{F2}}{l_3};$$

the first light transmission element is arranged as part of a wall of the flow channel;

a distance ($l_{F1}$) of the first light transmission element to the radiation source, in relation to the radiation source distance, is according to a relationship:

$$\frac{l_{F1}}{l_3} \leq 0.3;$$

the diaphragm element is arranged at or outside the flow channel with a ratio of a width extension ($l_B$) of the diaphragm element in relation to a width extension ($l_S$) radiation of the radiation source according to a relationship:

$$\frac{l_B}{l_R} \geq 0.5;$$

the width extension ($l_B$) of the diaphragm element in relation to the width extension ($l_S$) of the radiation of the radiation source and a width extension of the first detector array and the second detector array ($l_{D1,2}$) is based on ratios according to a relationship:

$$\frac{l_B}{l_S} \geq \frac{l_{D1,2}}{l_S},$$

whereby a range of overlap is obtained, in the flow channel for the light emission generated by the radiation source, between the first detector array and the second detector array.

2. A device in accordance with claim 1, wherein:
the radiation source is configured as a flat radiator, as a diaphragm radiator or as a radiation element configured with a planarly configured radiating surface or as a light-emitting diode configured with a planarly configured radiating surface;

the radiating surface is configured for a uniform radiation emission over the radiating surface; and the radiating surface of the radiation source is selected in a range of 2.0 mm$^2$ to 10.0 mm$^2$.

3. A device in accordance with claim 1, wherein:
the first detector element and the second detector element are arranged at a first distance ($l_1$) from the length axis in a range of 0.1 mm to 10.0 mm;

the first array bandpass filter element and the second array bandpass filter element are arranged at the first detector element and the second detector element at a second distance ($l_2$) from the length axis, extending between the first detector array and the second detector array in a range of 0.1 mm to 10.0 mm.

4. A device in accordance with claim 1, wherein the first array bandpass filter element and the second array bandpass filter element are configured for optical filtering of infrared light in a transmission range of a wavelength range of 2.5 μm to 14 μm.

5. A device in accordance with claim 1, wherein the first detector element and the second detector element are configured as pyrodetectors, bolometers, semiconductor detectors, thermopiles or thermocouples.

6. A device in accordance with claim 1, wherein:
a space area, between the first detector array, the second detector array and the diaphragm element and/or a space area between the diaphragm element and the second light transmission element and/or a space area between the radiation source and/or the optically reflecting element and the first light transmission element and/or a space area between the second light transmission element and one of the first detector array and the second detector array is filled with an optically transparent material, which has an optical refractive index n>1.

7. A device in accordance with claim 6, wherein the length $l_{F1}$, $l_{F2}$ and $l_{DB}$ are physical geometric length extensions or as physical optical length extensions with inclusion of optical refractive indices of optically transparent materials between the diaphragm element and the second light transmission element and/or the diaphragm element and one of the first detector array and the second detector array and/or the radiation source and the first light transmission element and/or the second light transmission element and one of the first detector array and the second detector array.

8. A device for determining a concentration of a gas component in an inhaled gas or in an exhaled gas of a living being, the device comprising:
a radiation source configured to radiate light as a light emission in a wavelength range of lambda1 ($\lambda 1$)=2.5 μm to lambda2 ($\lambda 2$)=14.0 μm;

an optically reflecting element configured te reflect light, the optically reflecting element being arranged opposite the radiation source;

a first detector array comprising a first detector element configured to detect radiation reflected by the optically reflecting element and a first array bandpass filter element arranged at the first detector element and which forms a detection surface for detecting radiation reflected by the optically reflecting element;

a second detector array comprising a second detector element configured to detect radiation reflected by the optically reflecting element and a second array bandpass filter element arranged at the second detector element and which forms a detection surface for detecting radiation reflected by the optically reflecting element;
a flow channel configured to guide the flow of a gas flow essentially at right angles to a length axis of the light emission;
a first light transmission element;
a second light transmission element, each of the first light transmission element and the second light transmission element being configured to be optically transparent for the light emission in the wavelength range of lambda1 ($\lambda 1$)=2.5 µm to lambda2 ($\lambda 2$)=14.0 µm;
a diaphragm element configured to guide a light beam from the radiation source to the detection surface of the first detector array and the detection surface of the second detector array; and
a control unit configured to control operation of the radiation source and for detecting signals of the first detector element and the second detector element, wherein:
one of the first array bandpass filter element and the second array bandpass filter element is configured to be optically transparent for infrared radiation, which is absorbed by a measured gas, wherein another one of the first array bandpass filter element and the second array bandpass filter element is configured as being optically transparent for infrared radiation which is not absorbed by the measured gas;
a reflection surface of the optically reflecting element is arranged at a reflection surface distance ($l_3$) from the detection surface of the first detector array and the detection surface of the second detector array;
a distance ($l_{F2}$) of the second light transmission element to the detection surface of the first detector array and the detection surface of the second detector array is related to the reflection surface distance ($l_3$) according to a relationship:

$$\frac{l_{F2}}{l_3} \geq 0.5;$$

a diaphragm element distance ($l_{DB}$) from the detection surface of the first detector array and the detection surface of the second detector array to the diaphragm element is based on ratios according to a relationship:

$$0 \leq \frac{l_{DB}}{l_3} \leq \frac{l_{F2}}{l_3};$$

the first light transmission element is arranged as part of a wall of the flow channel;
a distance $l_{F1}$ of the first light transmission element to the reflection surface of the optically reflecting element in relation to the reflection surface distance ($l_3$) is according to a relationship:

$$\frac{l_{F1}}{l_3} \leq 0.3;$$

the diaphragm element is arranged at or outside the flow channel with a ratio of a width extension ($l_B$) of the diaphragm element in relation to a width extension ($l_R$) of the optically reflecting element according to a relationship:

$$\frac{l_B}{l_R} \geq 0.5;$$

and
a ratio for the width extension ($l_B$) of the diaphragm element in relation to the width extension ($l_R$) of the optically reflecting element and a width extension of the first detector array and the second detector array ($l_{D1,2}$) is according to a relationship:

$$\frac{l_B}{l_R} \geq \frac{l_{D1,2}}{l_R},$$

whereby a range of overlap is obtained, in the flow channel for the light emission generated by the radiation source, between the first detector array and the second detector array.

9. A device in accordance with claim 8, wherein:
the radiation source is configured as a spotlight or as a light-emitting diode radiating in a punctiform shape with a radiating surface directed toward the optically reflecting element essentially with a width radiation angle of 80° to 170° and is configured for uniform radiation in a direction of the optically reflecting element; and
an area of the radiating surface of the radiation source is selected to be in a range of 0.05 mm² to 1 mm².

10. A device in accordance with claim 8, wherein the optically reflecting element is configured with a surface structure for a uniform distribution of the reflected light, between the first detector array and the second detector array.

11. A device in accordance with claim 8, wherein:
the first detector element and the second detector element are arranged at a first distance ($l_1$) from the length axis in a range of 0.1 mm to 10.0 mm;
the first array bandpass filter element and the second array bandpass filter element are arranged at the first detector element and the second detector element at a second distance ($l_2$) from the length axis, extending between the first detector array and the second detector array in a range of 0.1 mm to 10.0 mm.

12. A device in accordance with claim 8, wherein the first array bandpass filter element and the second array bandpass filter element are configured for optical filtering of infrared light in a transmission range of a wavelength range of 2.5 µm to 14 µm.

13. A device in accordance with claim 8, wherein the first detector element and the second detector element are configured as pyrodetectors, bolometers, semiconductor detectors, thermopiles or thermocouples.

14. A device in accordance with claim 8, wherein:
a space area, between the first detector array and the second detector array and the diaphragm element; and/or
a space area between the diaphragm element and the second light transmission element; and/or
a space area between the radiation source and/or the optically reflecting element and the first light transmission element; and/or a space area between the second light transmission element and one of the first detector array and the second detector array, is filled with an optically transparent material, which has an optical refractive index n>1.

15. A device in accordance with claim 14, wherein the length $l_{F1}$, $l_{F2}$ and $l_{DB}$ are physical geometric length extensions or as physical optical length extensions with inclusion of optical refractive indices of optically transparent materials between the diaphragm element and the second light transmission element and/or the diaphragm element and one of the first detector array and the second detector array and/or the radiation source or the optically reflecting element and the first light transmission element and/or the second light transmission element and one of the first detector array and the second detector array.

\* \* \* \* \*